United States Patent

Ulrich

Patent Number: 6,024,575

Date of Patent: Feb. 15, 2000

[54] ARRANGEMENT FOR MONITORING PHYSIOLOGICAL SIGNALS

[75] Inventor: Paul Christopher Ulrich, Medfield, Mass.

[73] Assignee: Paul C. Ulrich, Cambridge, Mass.

[21] Appl. No.: 09/106,827

[22] Filed: Jun. 29, 1998

[51] Int. Cl.[7] .......................... G09B 19/00; G09B 23/28
[52] U.S. Cl. ...................... 434/236; 434/262; 128/905
[58] Field of Search ........................... 36/141; 128/905; 434/236, 262; 600/306, 544, 545, 546, 547, 548, 549, 552, 557

[56] References Cited

U.S. PATENT DOCUMENTS

| | | | |
|---|---|---|---|
| 3,731,674 | 5/1973 | Parvin ........................................ | 600/30 |
| 3,753,433 | 8/1973 | Bakerich et al. ........................ | 600/545 |
| 3,855,998 | 12/1974 | Hidalgo-Briceno ..................... | 600/545 |
| 3,870,034 | 3/1975 | James ....................................... | 600/574 |
| 3,942,516 | 3/1976 | Glynn et al. . | |
| 4,690,142 | 9/1987 | Ross et al. . | |
| 4,802,463 | 2/1989 | Rojas ........................................ | 601/70 |
| 5,304,112 | 4/1994 | Mrklas et al. ............................ | 600/27 |
| 5,409,011 | 4/1995 | Alexeev et al. ......................... | 600/547 |
| 5,592,759 | 1/1997 | Cox .......................................... | 36/141 |
| 5,595,488 | 1/1997 | Gozlan et al. ........................... | 434/236 |
| 5,608,599 | 3/1997 | Goldman ............................... | 361/283.1 |
| 5,679,004 | 10/1997 | McGowan et al. ..................... | 434/247 |
| 5,743,744 | 4/1998 | Cassily et al. . | |
| 5,792,067 | 8/1998 | Karell ..................................... | 600/534 |
| 5,807,114 | 9/1998 | Hodges et al. .......................... | 434/236 |
| 5,836,899 | 11/1998 | Reilly ...................................... | 601/46 |
| 5,844,862 | 12/1998 | Cocatre-Zilgien ....................... | 368/10 |
| 5,862,803 | 1/1999 | Besson et al. ........................... | 600/508 |
| 5,894,687 | 4/1999 | Lin .......................................... | 36/141 |

OTHER PUBLICATIONS

Thought Technology 1998 Brochure for GSR2, GSR/Temp 2X, published in Canada and USA.

Matsushita (Panasonic) 1994 Product Leaflet, sold in Brookstone stores, USA, Dual Action Shiatsu Vibrating Foot Massager.

Innovation Shop 1998 Shiatsu Slippers with electric nodes as shown on Web site www.bam.net/innovation/misc.html, USA.

Sharper Image May 1998 Catalogue, p. 24, Harmony Sleep Companion with Silent Arm, USA Alarm.

Sharper Image May 1998 Catalogue, p. 20, Contour Concept Massager, USA.

Sharper Image May 1998 Catalogue, p. 39, Power Flow Height–Enhancing Insoles, USA.

Sharper Image May 1998 Catalogue, p. 83, IntelliSense Automatic Blood Pressure Monitor, USA.

Sharper Image May 1998 Catalogue, p. 85, Rolling Foot Massager, USA.

Sharper Image May 1998 Catalogue, p. 86, Computerized Shiatsu, USA.

(List continued on next page.)

*Primary Examiner*—Robert A. Hafer
*Assistant Examiner*—John Edmund Rovnak
*Attorney, Agent, or Firm*—Werner Ulrich

[57] ABSTRACT

Insertable insoles of flexible air-injected elastomer material with one or both said insoles containing a lithium-battery power supply (27), a microprocessor with an internal timer, an analog/digital converter, and an actuator (28), connected by at least one wire (29) to a plurality of electronic sensors (12) wrapped around the toes of the foot. The actuator vibrates a plurality of raised nodes (20) on the insole(s) with the speed and intensity of vibrations in either direct or inverse response to the level of stress experienced, as measured by physiological signals such as galvanic skin response. A thin foam lining covers the top surface of the elastomer material and cushions the feet. In addition, a washable, stretchable nylon lining (30) separates the foam from the sole of the bare foot, but a small elastic hole (32) near the toes permits said wire and sensors to extend to the skin of the toes. Once either or both of the insoles are attached to the toes, the feet together with the insoles are inserted into a pair of socks or stockings.

20 Claims, 3 Drawing Sheets

OTHER PUBLICATIONS

J. Healey & R.W. Picard, "StartleCam: A Cybernetic Wearable Camera", 1998 unpublished paper, pp. 1–10, Cambridge, USA.

Hammacher Schlemmer Summer 1998 Catalogue, p. 33, Foot Cushioning Gel Socks, USA.

Hammacher Schlemmer Summer 1998 Catalogue, Massaging Sport Sandals p. 63, USA.

Conscious Living Foundation 1998 Web Site, www.cliving.org, Stress Computer, USA.

J. Healey & G. Gould, Affective Jewelry and Other Affective Accessories, 1997 Web Site: vismod.www.media.mit.edu/vismod/, USA.

Fig. 1
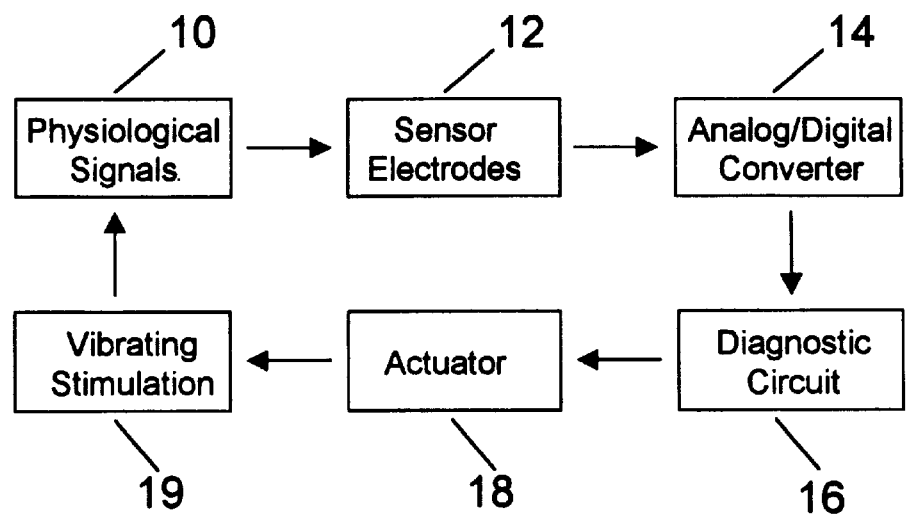
Fig. 2-A
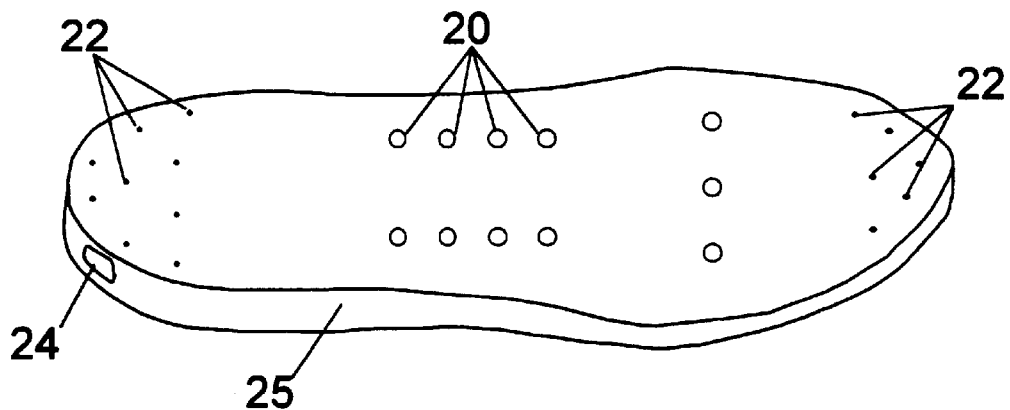

Fig. 2-B
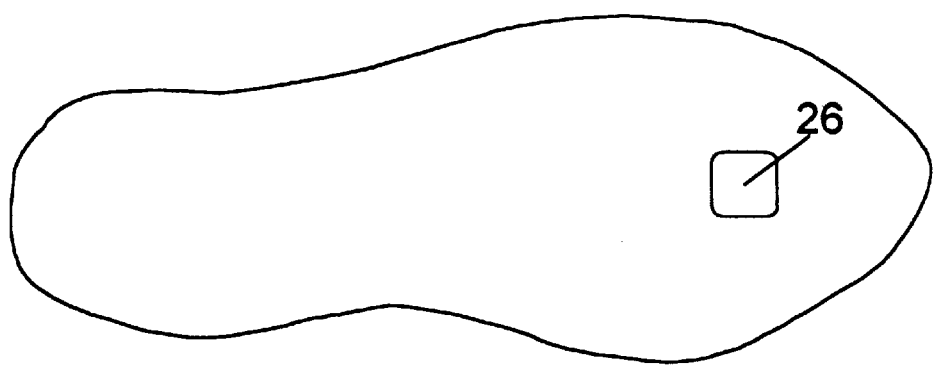
Fig. 2-C
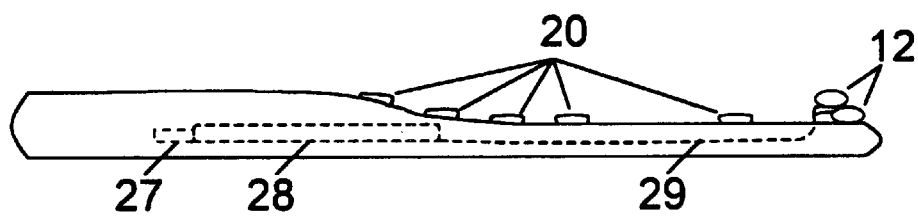
Fig. 3
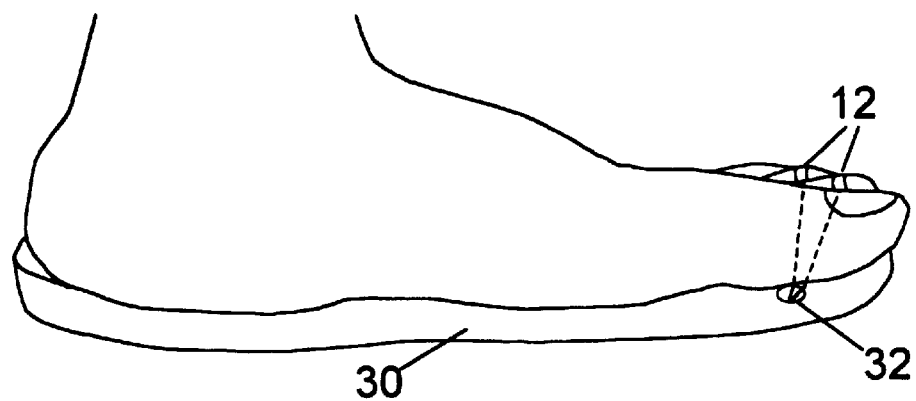

Fig. 4-A
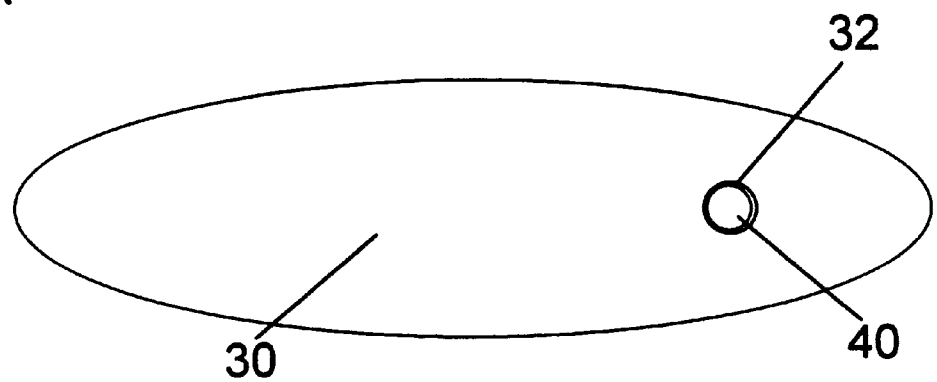
Fig. 4-B
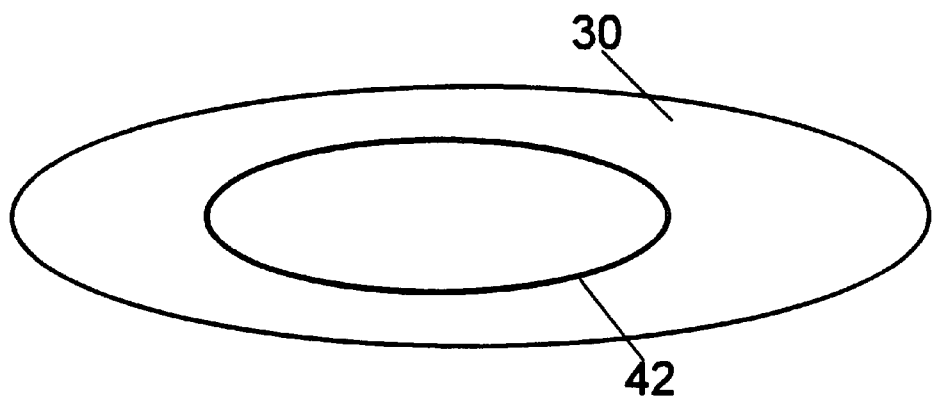

6,024,575

ARRANGEMENT FOR MONITORING PHYSIOLOGICAL SIGNALS

BACKGROUND—FIELD OF INVENTION

This invention relates to biofeedback, specifically to an improved mechanism for providing physiological information to a user or to other persons in such a way as to be readily discernible only to the intended recipient of the information.

BACKGROUND—DESCRIPTION OF PRIOR ART

Physicians have traditionally used biofeedback devices to help train patients in techniques for monitoring and controlling physiological signals during visits to a clinic or doctor's office. Computers with electronic sensors attached to the patient display visual or auditory images that vary in intensity or form to reflect changes in the underlying signals being monitored. Patients try to reduce their stress levels, indicated by the displayed signals, through a variety of relaxation techniques. Portable stress-control devices have also been available for use at home. The devices for home use rely on the same visual and audio feedback as the larger, more complex devices used under a clinician's supervision.

Recent advances in the miniaturization of electronics have led to wearable biofeedback devices such as visual wristwatch displays or visual electronic monitors the size of credit cards that can be held in, and attached to, the hand. In the prior art of mechanical vibrations as indicators of information, many cell phones and pagers use vibrations to indicate incoming calls. Likewise, one vendor of innovative products sells a silent alarm wrist watch to wake users via mechanical vibrations during episodes of snoring. There are mechanically vibrating massage products for the feet and other parts of the body but none uses input from physiological signals. There is also publicly available and recent university research with a prototype model for sensors worn in the shoe to measure physiological signals, but the models rely on wireless transmission to convey visual displays to remote computer screens rather than mechanical vibrations to remote sites on the wearer's body or the body of another person.

SUMMARY OF THE INVENTION

Applicant has analyzed the prior art of biofeedback arrangements and has recognized that all have the common disadvantage that the users are not the only persons who may receive, or intercept biofeedback signals; this destroys the important privacy of the biofeedback training process. Applicant has overcome this disadvantage, and made a contribution over the prior art by an arrangement which uses mechanical vibrations to provide a feedback signal to the user, and providing the feedback signal only when a sensed signal exceeds a threshold, or providing the feedback signal only when the sensed signal is less than said threshold. Advantageously, only the feedback user receives this feedback signal. Advantageously, mechanical vibrations are not provided continuously, but only when the sensed signal is in proper relation to the threshold.

In one preferred embodiment, the threshold can be adjusted, using, for example, a potentiometer by the user. Advantageously, this arrangement allows users with different ranges of sensed signals to adjust when they will receive vibrations. In one preferred embodiment, the vibrations are directed to the foot. Advantageously, the foot is particularly sensitive to vibration signals, and the source of the vibrations can be hidden from outsiders.

Accordingly, several objects and advantages of the present invention are:

(a) to provide physiological signals and biofeedback training through a small, wearable device that can be worn throughout the day during a variety of activities.

(b) to provide physiological signals and biofeedback training to enable the user to link the stress experienced directly with activities or thoughts as they occur rather than in a controlled environment.

(c) to provide physiological signals and biofeedback training in a manner that does not distract the user from other tasks in which he or she is engaged.

(d) to provide physiological signals and biofeedback training in a discreet, unobtrusive way that neither alerts other persons to the use of the device nor disturbs them.

(e) to provide physiological signals and biofeedback training in environments of low light or high noise when audio or visual displays are difficult or hard to detect.

(f) to provide physiological signals and biofeedback training in a vibrating, massage-like manner that helps to relax the user and reduce the stress that is being monitored.

(g) to provide physiological signals and biofeedback training, as needed, in reverse correlation to the stress experienced under conditions when alertness is required and the subject is in danger of dozing off.

(h) to provide physiological signals and biofeedback training, as needed, in positive correlation to the stress experienced under conditions when relaxation is required and the subject is in danger of being overly stressed.

Further objects and advantages of my invention will become apparent from a consideration of the drawings and ensuing description.

DRAWING FIGURES

In the drawings, closely related figures have the same number, but different alphabetic suffixes.

FIG. 1 shows a closed-loop flowchart of the method for discreetly monitoring physiological signals via a wearable, vibrating biofeedback device.

FIGS. 2A to 2C show various aspects of the left foot's insertable insole.

FIG. 3 shows the left foot's placement on the insertable insole and attachment to ring sensors at the toe.

FIG. 4A and 4B show various aspects of the nylon slipcover for the insertable insole.

REFERENCE NUMERALS IN DRAWING

| | |
|---|---|
| 10 physiological signals | 12 sensor electrodes |
| 14 analog/digital converter | 16 diagnostic circuit |
| 18 actuator | 19 vibrating stimulation |
| 20 raised nodes | 22 airhole perforations |
| 24 on/off connector switch | 25 side of insole |
| 26 alternative on/off switch location | 27 lithium battery |
| 28 microprocessor with actuator | 29 wire |
| 30 slip cover | 32 slip-cover hole |
| 40 elastic band for slip-cover hole | 42 elastic band |

DESCRIPTION—ILLUSTRATIVE EMBODIMENT, FIGS. 2 TO 7

FIG. 2A (top view), FIG. 2B (bottom view), and FIG. 2C (side view) illustrate typical embodiments of the insertable insole for the left foot. A matching insole mold without sensors or electronics for the right foot should be worn at the same time. The thickness of the side of the insole 25 tapers from about two centimeters at the heel to about 0.5 centimeters at the toe. The insole is made of a flexible elastomer such as ethylene vinyl acetate, silicone, or plasticized polyurethane, that has been injected with air. The resulting airpockets lighten the material and link to cooling airhole perforations 22 along the heel and toe. Two rows of raised nodes 20 run along the middle of the surface of the insole with a third row closer to the toes of the same insole. The nodes of the left insole protrude above the top surface of the sole by about 0.5 centimeters. A thin layer of frelene or polynylon lined foam covers and cushions the surface of the insole. Toward the back heel of the insole is an on/off connector switch 24, with a face flush to the edge of the sole. FIG. 2B shows an alternative location for the on/off switch 26. Embedded within the insole are a lithium battery 27, microprocessor or microcontroller with actuator 28 and a wire 29 connecting to the sensors 12 that are looped around two toes of the foot. FIG. 3 shows how the wire to the sensors extends through a hole 32 at the front end of the washable nylon slip-cover 30 encasing the insole. FIGS. 4 and 5 show the top and bottom views of the stretchable slip cover and the elastic band 40 around the hole for fitting the wires and sensors as well as the band 42 for stretching the cover onto the insole. Once either or both insoles are attached to the toes, the feet together with the insoles are inserted into a pair of socks or stockings.

Operation—Main Embodiment, FIG. 1

FIG. 1 shows a closed loop flowchart to illustrate the operation of the biofeedback device. Fluctuations in physiological signals 10 such as galvanic skin response (GSR), an indication of stress, are sensed by the sensors 12 wrapped in place around the toes. The sensors pass the analog signal to an analog to digital converter 14. The digital output of the converter is sent to a diagnostic circuit 16 of the microprocessor, which passes a digital signal to an actuator or transducer 18 causing the nodes and insole to vibrate. The speed and intensity of vibrating stimulation 19 varies with the measure of stress experienced, as indicated by changes in the GSR signal. The vibrations serve both to indicate the level of stress experienced and to help reduce the stress in a self-calibrating, closed-loop manner. In addition, the microprocessor has an internal timer to limit the vibrations at any one time to thirty minutes, the recommended limit that anyone should be exposed to massage vibrations during an uninterrupted period. The electronic components can also include a potentiometric device for calibrating the sensitivity of the device. The potentiometer, which is calibrated to, and/or by each individual, sets a threshold level, below which vibrations do not occur. This is especially desirable for this type of biofeedback system since prolonged periods of vibrations are undesirable. For some persons, this level will be set very high so that the device provides a vibrating alert only during times of the most extreme stress.

Description and Operation—Alternative Embodiments

In alternative embodiments, the wearable, vibrating device can be worn beneath clothing at a different part of the wearer's body such as the arm, leg, or trunk, and the sensors can be attached to nearby skin. Alternatively, a wireless connection can separate the sensors and diagnostic circuit on one part of the body from the actuator and mechanically vibrating device, attached either to another part of the wearer's body or to a concealed part of the body of another person responsible for monitoring the physiological signals of the wearer.

Conclusion, Ramifications, and Scope

The wearable, vibrating biofeedback device provides a discreet, unobtrusive mechanism for monitoring one's level of stress throughout the day, in a variety of environments, without distraction to the user or others, and in a manner that can either help the user to relax and reduce the stress through vibrations or to awaken the user in situations where continued alertness is necessary.

While the above description of the main embodiment contains many specificities, these should not be construed as limitations on the scope of the invention, but rather as an exemplification of one preferred embodiment thereof. Many other variations are possible. For example, to prevent the user from dozing off, the microprocessor can be programmed to cause vibrations in inverse relation to the degree of stress experienced. In one possible embodiment, such an arrangement can actuate mechanical vibrations to awaken the driver of an automobile, truck, or other heavy equipment if that person's galvanic skin response drops below a certain threshold. In another possible embodiment, the biofeedback signals can be sent not to the user but via wireless transmission to other persons who might wear vibrating apparatus and have a need to monitor either the level of stress or alertness experienced by the subject.

A simple microcontroller without analog/digital converter can be used to operate the actuator simply through the analog pulse amplified from the sensors. Either the raised nodes or the entire insole together with nodes can be made to vibrate. The vibrations of individual nodes or groups of nodes can be programmed to move in a variety of motions and techniques comprising Shiatsu massage, Tsubo massage, simple variation of speed and intensity of massage, or any of the five basic categories of soft tissue manipulation in traditional European methods: gliding strokes, kneading, rubbing, percussion, and vibration. Nodes can be aligned to correspond with reflexology points on the sole of the foot. A heating element and a thermistor for monitoring changes in skin temperature can be added if skin temperature is tracked as the indicator of stress level. Alternatively the sensors can monitor other physiological signals such as heart rate, blood pressure, electromyography, and electroencephalography, and electro-oculography. The switch to turn the device on and off can be a push button at the side of the heel, a connector strip along the side, or a connector at the sole, activated by a rapid double click on the ground. The biofeedback sensors can be attached to the toes or the bottom of the feet. The insole can be of varying thickness from as thin as possible to as much as an inch or so. The sensors, microprocessor, and vibrating nodes can be in both insoles rather than just one. The insole can have a fastener and thin elastic strap for wrapping across the top of the foot, directly above the arch, to hold the insole more firmly in place against the sole and to facilitate insertion of feet and insoles into socks or stockings. The entire apparatus can also be worn elsewhere on the body under one's clothing, for example, as a vibrating bracelet with sensors attached to the arm or on the lower back. The feet were chosen because both the hands and toes are most sensitive to touch and the galvanic skin response.

Accordingly, the scope of the invention should be determined not by the embodiments illustrated, but by the appended claims and their legal equivalents.

I claim:

1. A method of conveying physiological information, comprising the steps of:

a. detecting physiological signals representing said physiological information;

b. converting said signals into mechanical vibrations that vary in a correlated manner in response to said signals, provided said signals exceed a threshold;

c. providing said mechanical vibrations by discreet means, readily discernible only to an intended recipient of said information; and d. providing said mechanical vibrations by unobtrusive means, thereby allowing said intended recipient to move freely about while monitoring said information in the course of a variety of everyday activities.

2. The method of claim 1, wherein said method detects said signals using at least one electronic sensor as a means of measuring at least one of a plurality of inaudible physiological signals comprising galvanic skin response, skin temperature, heart rate, blood pressure, electromyography, electroencephalography, and electro-oculography.

3. The method of claim 2, wherein said at least one electronic sensor is attached to a part of a foot, or to other parts of the body beneath clothing of said wearer.

4. The method of claim 2, wherein said method actuates said mechanical vibrations by means of a diagnostic circuit.

5. The method of claim 4, wherein said diagnostic circuit comprises a microprocessor.

6. The method of claim 2, further including a wireless means of transmitting to a remotely situated means of actuating the source of said mechanical vibrations.

7. The method of claim 2, further comprising the step of:
adjusting said threshold in conformance with requirements of said intended recipient.

8. The method of claim 2, wherein said method provides said mechanical vibrations by means of separate and independent vibration of a plurality of nodes.

9. The method of claim 8, wherein said mechanical vibrations comprise a plurality of motions and techniques including gliding strokes, kneading, rubbing, percussion, and varying speed and intensity of movement.

10. The method of claim 8, wherein said method involves the massage of reflexology points along the soles of the feet.

11. A device for providing physiological information comprising:

a. at least one electronic sensor for measuring physiological signals of a wearer; and b. means for providing information on said signals to said wearer or to other persons by means of mechanical vibrations;

c. means for providing mechanical vibrations to said wearer or another person;

d. wherein said mechanical vibrations vary in a correlated manner in response to said signals, provided that said signals exceed a threshold;

e. wherein said means for providing mechanical vibrations provide said mechanical vibrations so as to be readily discernible only to the recipient of said information; and f. wherein said means for providing mechanical vibrations are unobtrusive, allowing said intended recipient to move freely about while monitoring said information in the course of a variety of everyday activities.

12. The device of claim 11, wherein said at least one electronic sensor measures changes in at least one of a plurality of inaudible physiological signals comprising galvanic skin response, skin temperature, heart rate, blood pressure, electromyography, electro-encephalography, and electro-oculography.

13. The device of claim 12, wherein said at least one electronic sensor is attached to parts of the feet or to other parts of the body beneath clothing of said wearer.

14. The device of claim 12, wherein said means for providing said mechanical vibrations is actuated by means of a diagnostic circuit.

15. The device of claim 14, wherein said diagnostic circuit comprises a microprocessor.

16. The device of claim 12, further including a wireless means for transmitting to a remotely situated means for actuating the source of said mechanical vibrations.

17. The device of claim 12, further comprising means for adjusting said threshold in conformance with requirements of said intended recipient.

18. The device of claim 12, wherein said means for providing mechanical vibrations comprises means for providing separate and independent vibration of a plurality of nodes.

19. The device of claim 18, wherein said vibration comprises a plurality of motions and techniques including gliding strokes, kneading, rubbing, percussion, and varying speed and intensity of movement.

20. The device of claim 18 wherein said device involves the massage of reflexology points along the soles of the feet.

* * * * *